United States Patent [19]

Luther et al.

[11] Patent Number: 4,874,373
[45] Date of Patent: Oct. 17, 1989

[54] DIP FORMED CATHETER AND ASSEMBLY

[76] Inventors: Ronald B. Luther, 530 Kings Rd., Newport Beach, Calif. 92663; Billy H. Hannaford, 1822½ Newport Blvd., #372, Costa Mesa, Calif. 92627

[21] Appl. No.: 21,135
[22] Filed: Mar. 3, 1987
[51] Int. Cl.$^4$ ............................................. A61M 5/18
[52] U.S. Cl. .................................... 604/164; 604/166; 604/168; 604/283; 604/900; 264/301
[58] Field of Search ............... 604/900, 280, 283, 164, 604/166, 168; 264/301

[56] References Cited

U.S. PATENT DOCUMENTS

| 2,112,666 | 3/1938 | Fennell | 604/280 |
|---|---|---|---|
| 3,204,634 | 9/1965 | Koehn. | |
| 3,375,310 | 3/1968 | Koehn. | |
| 3,500,828 | 3/1970 | Podhora | 604/900 X |
| 3,859,998 | 1/1975 | Thomas et al. | 604/900 X |
| 4,046,144 | 9/1977 | McFarlane | 604/168 |
| 4,193,400 | 3/1980 | Loveless et al. | 604/168 |
| 4,250,881 | 2/1981 | Smith | 604/166 |
| 4,371,686 | 2/1983 | Yamamoto et al. | 528/76 |
| 4,373,009 | 2/1983 | Winn | 604/280 X |
| 4,610,671 | 9/1986 | Luther | 604/168 |
| 4,781,703 | 11/1988 | Walker et al. | 604/264 |

FOREIGN PATENT DOCUMENTS 2150938  7/1985  United Kingdom ............... 604/280

OTHER PUBLICATIONS

Introducing the 'Intraducer', 1/10/1977.

Primary Examiner—Robert E. Garrett
Assistant Examiner—Carl D. Price
Attorney, Agent, or Firm—Willie Krawitz

[57] ABSTRACT

A catheter constructed of a polymeric material that is produced by dip coating over a mandrel or needle, is disclosed. The catheter which is formed is then removed by expansion upon contact with a liquid containing water, or by applied manual pressure. The integrally formed assembly has fewer component parts and has a more accurately shaped catheter tip and tapered end.

21 Claims, 4 Drawing Sheets

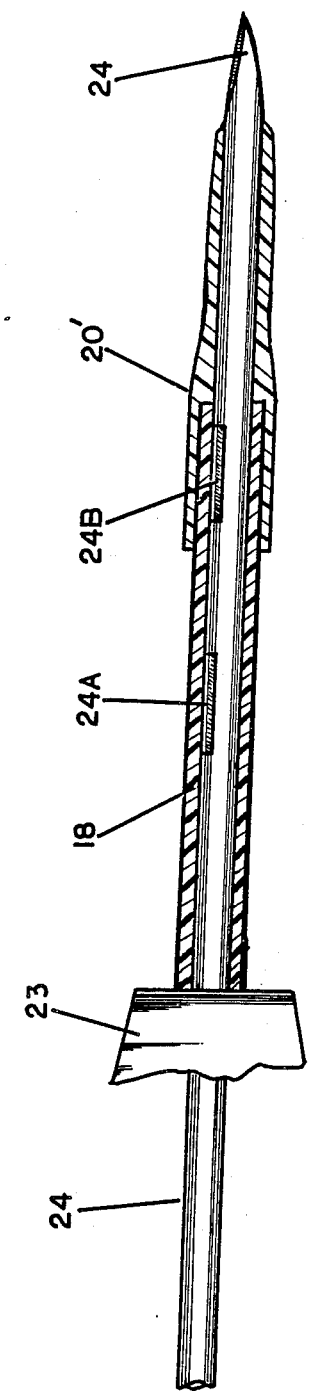

DIP FORMED CATHETER AND ASSEMBLY

BACKGROUND OF THE INVENTION

This invention relates to a new and improved catheter for use with needles, the catheter being formed by a dip coating process.

Catheters formed by conventional extrusion processes have various drawbacks. For example, extrusion formed catheters must be end shaped to avoid trauma when inserted into a patient's vein. In addition, these catheters lack bore accuracy and tend to undergo a decrease in molecular weight or degradation of molecular structure upon extrusion. The combined effects cause a reduction in compression strength; consequently, upon insertion, these prior art catheters can buckle.

It would be desireable to produce an integrally formed needle and catheter assembly, or a hub and catheter assembly in a single step.

It would be desireable to provide a needle and catheter assembly, also, in which the catheter fits tightly over the needle, but which can be quickly and easily separated.

It would be further desireable to be able to form a catheter in many desired shapes.

It would be also desired to reduce or eliminate the amount of configuration necessary to shape the end of a catheter after it has been formed.

In addition, it would be desireable to form a catheter having greater compression strength than extrusion or injection molded catheters of corresponding material.

THE INVENTION

According to the invention, there is provided a manufacturing process for producing an over-the-needle catheter, an assembly of a catheter and a needle, an assembly of an integrally formed hub and catheter, and combinations thereof.

Preferred materials of construction for the dip formed catheters of this invention are hydrophilic polymers that expand upon contact with water. Publications disclosing hydrophilic polymers include: U.S. Pat. Nos. 3,822,238; 3,975,350; 4,156,066; 4,156,067; 4,255,550; 4,408,023; 4,424,305; 4,439,583; 4,439,584; 4,439,554; and, 4,439,558. Useful polymeric compositions are disclosed in U.S. Pat. No. 4,408,023 which describes a polyurethane component, a polyoxyethylene glycol component, and a low molecular weight glycol such as diethylene glycol and/or dipropylene glycol. Variations in the molecular weight and/or dipropylene glycol contribute hydrophilic properties to the polymeric composition. Variations in physical and chemical properties of the polymer including water uptake, expansion characteristics, absorption of electrolytes and body fluids, the passage of gases, etc., are produced thereby.

Consequently, a time releases medication may be incorporated into the polymer. The medication is subsequently leached out by passage of the I.V. fluid, or by fluids in body tissue, including blood. This leaching provides small amounts of a high concentration of a disinfectant and/or bacteriostat, fungicide, antibiotic, etc., at the puncture site. Leaching out cannot be duplicated with present day catheters which are manufactured of non-leachable material such as polyvinyl chloride, teflon, polyurethane, polyethylene, etc.

The hydrophilic polymers can be dip coated onto a mandrel or needle, or formed as an attachment to a hub with a close degree of size conformation, or less than about 1 mil. By comparison, extrusion formed catheters have a size conformation of about ±2 mils. One type of such prior art extrusion formed catheter using the above hydrophilic materials is described in U.S. Pat. No. 4,610,671 to Ronald B. Luther.

Consequently, there is far less tendency for catheters of this invention to become separated from an associated needle or hub. In addition, dip forming the catheter does not reduce the molecular weight of the polymer or degrade its structure; hence its resistance to compression is improved.

Following dip forming onto say, a needle, the catheter will expand upon contact with liquid (e.g. blood) when it has been inserted into a patient. This expansion enables the catheter and needle to be easily separated.

The present process for manufacturing a catheter-hub-needle assembly produces an integrally formed device, whereas the prior art requires say, a six or seven piece unit. The manufacturing process of this invention also provides a more precise control of the tip shape and taper of the catheter.

BRIEF DESCRIPTION OF THE DRAWINGS

FIG. 3 is a cross sectional view in side elevation showing a plastic tube carried by a needle, the tube connecting a hub and a dip formed catheter; and, FIGS. 4 and 5 are external views in side elevation showing the dip coating of a plurality of mandrels with a polymeric solution and the withdrawal from the mandrels of formed catheters, respectively.

DESCRIPTION OF THE PREFERRED EMBODIMENTS

Figure 1:
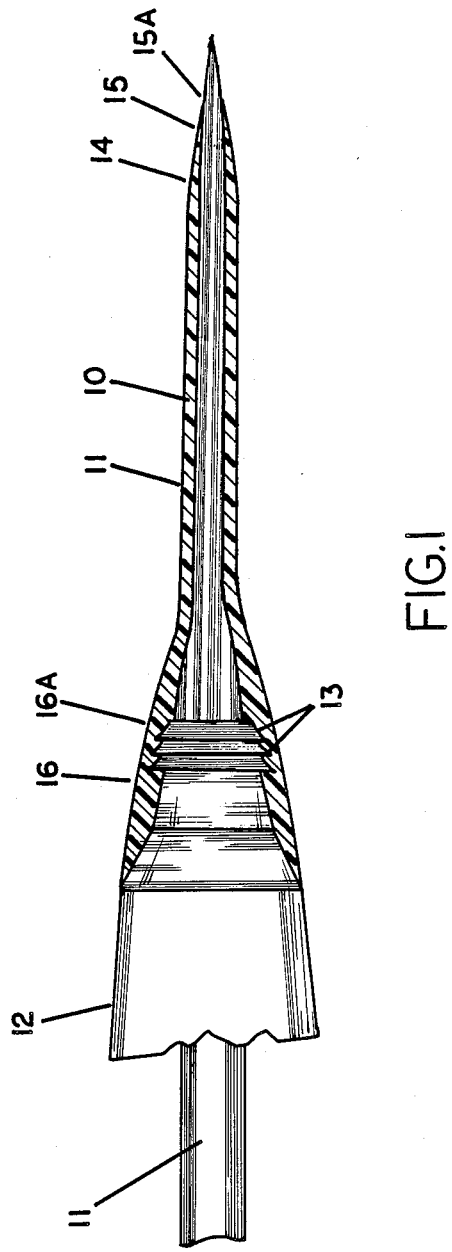
FIG. 1 is a cross-sectional view in side elevation showing an integrally formed luer-lock hub and catheter, the latter having been dip formed over a mandrel.

A dip formed catheter 10 according to the invention is shown in FIG. 1, mounted on a mandrel 11, and over a luer-lock hub 12. A plurality of external serrations 13 are defined on the external surface of the hub to secure the catheter thereto. The distal end 14 of the catheter is configured to provide an inclined portion 15 which defines a leading edge 15a of minimal thickness. This configuration is produced by dip forming the catheter onto the mandrel and hub, and then withdrawing the mandrel.

The proximal end 16 of the dip formed catheter defines an enlarged portion 16a which produces a large surface area of contact between the hub and catheter. The combined effect of the large surface area and the serrations 13 enable the user to grasp and insert the device and needle into a patient without the hub and catheter becoming separated. Also, the hub and catheter are strongly bonded together by the dipping process, and this further reduces the possibility of the hub and catheter becoming separated when in use. The mandrel is removed and the needle is inserted into th catheter while it is still in the expanded state. Upon drying, the catheter will contract about the needle and form a good shrink fit therewith. Alternatively, the catheter, following removal of the mandrel, can be simply dried and stored. The catheter is subsequently expanded by contact with water to enable insertion of a needle therethrough.

Figure 2:
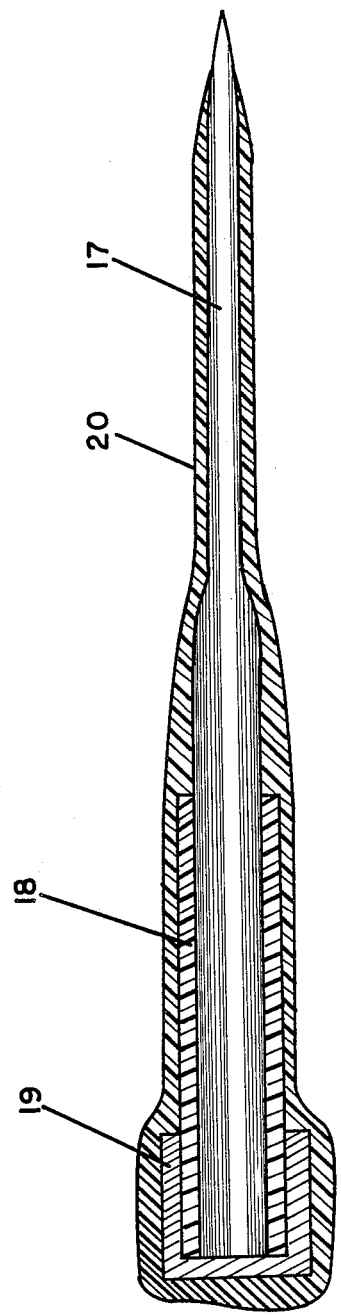
FIG. 2 is a cross sectional view in side elevation showing a plastic tube fitting over a mandrel and a dip coated catheter formed over the plastic tube and the mandrel.

FIG. 2 illustrates another embodiment of this invention and shows a mandrel 17 bearing a plastic connector tube 18 of say, polyurethane encased in a housing 19. The mandrel and plastic connector tube are then dip coated with an expandable hydrophilic polymer 20. The housing 19 and polymer 20 are then cut away to expose the plastic connector tube 18, and the mandrel is removed.

As shown in FIG. 3, the connector tube 18 and bonded catheter 20 are then joined or attached to a hub 23 by a bonding operation or by press fitting together. This arrangement enables a long, flexible and clear plastic tube to replace an equivalent length to dip formed catheter. A needle 24 of suitable size is then inserted through the catheter. The needle 24 is shown provided with one or more notches 24a, 24b to indicate blood flashback almost when it occurs.

Usually, flashback in these types of devices is first shown at the hub or proximal and; hence the present system of determining blood flashback represents a distinct improvement over the prior art.

Figure 5:
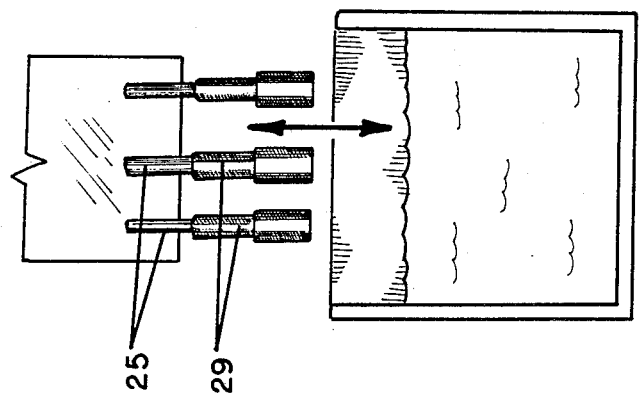
Figure 4:
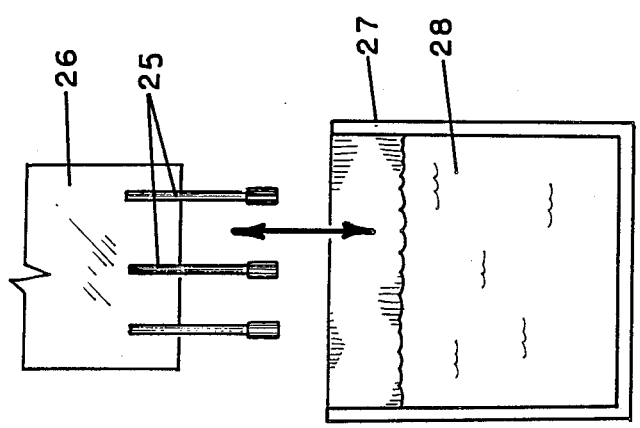

FIGS. 4 and 5 illustrate a dip coating apparatus and process which may be employed to produce catheters and assemblies of this invention. A plurality of mandrels 25 are mounted on a support 26 and are immersed into a container 27 containing a solution 28 of the desired polymer. When removed from the solution 28, the mandrels are coated with the polymer 29, which ultimately becomes the catheters. The polymer ends are then cut to open the catheter at the closed end, and the catheter is then dried and stored for use. In the dried state, the catheter should have a hardness exceeding about 90 SHORE A.

Typically, catheters manufactured by the process of this invention may have bore sizes about 12–30 gauge, a wall thickness of about 5–15 mils, and lengths of about ½"–6".

A plurality of say 4–5 dipping coats are applied, each dipping time being about 6–7 minutes, at room temperature. Each coating is then air dried at about 70° F.–225° F. Finally, the hub and catheter assembly are immersed in water causing the catheter to expand. This enables the assembly to be removed from the mandrel, in the direction shown by the arrows in FIG. 5. If necessary, the final configuration may be obtained by a minor cutting, grinding or abrasion step.

It will be apparent that various embodiments of the device may be produced while still remaining within the scope of the invention.

For example, a radiopaque material may be encapsulated between the first and last dip coats over the needle or mandrel. Also, different layers of polymers may be applied using the same or different solvents for the polymers. Furthermore, a balloon section may be formed by adding a special coating on one of the layers. If desired, the catheter itself may be formed with a closed, rounded tip which can be inserted through-the-needle. This configuration enables the catheter to be inserted more easily through a vein, and enables sterility to be better maintained.

Obviously, polymers other than hydrophilic types may be used in the dip coating process, such as polyvinyl chloride, nylon and polyurethane. A slip agent coating the mandrel may be used to assist in removing the dip coated polymer from the mandrel. The process of this invention provides an integrated (and hence less expensive) process for producing an assembly of a hub, needle and catheter, an over-the-needle catheter, and combinations thereof.

We claim:

1. A catheter and needle assembly formed by a process of:
   a. dip coating a mandrel from a solution of an expandable, hydrophilic polymer;
   b. expanding the polymer coating away from the mandrel by contacting the polymer with a liquid containing water;
   c. removing the polymer coating in the form of a catheter from the mandrel, the catheter defining a longitudinal cavity approximating the shape of the mandrel; and,
   d. inserting a needle into the longitudinal cavity of the catheter and drying the catheter to contract the catheter about the needle;
      the catheter being expandable due to contact with a liquid containing water, and thereby being removable from the needle.

2. The assembly of claim 1, in which the catheter provides a bore size of about 12–30 gauge, a wall thickness of about 5–15 mils, a length of about ½"–6", and a hardness of about at least 90 SHORE A in the dry state.

3. The assembly of claim 2, in which the catheter provides a size conformation with the needle of less than about 1 mil.

4. The assembly of claim 1, in which the catheter is connected by a flexible, plastic tube to a luer-lock hub.

5. The assembly of claim 5, in which the plastic tube is constructed of a clear material.

6. The catheter and needle assembly of claim 1, in which a time release medication is incorporated into the catheter.

7. The catheter and needle assembly of claim 6, in which said medication may be subsequently leached out of the catheter by passage of fluid, the said medication comprising a disinfectant, bacteriostat, fungicide, and antibiotic.

8. The catheter and needle assembly of claim 7, in which said fluid comprises I.V. fluid, body tissue fluid and blood.

9. The catheter and needle assembly of claim 1, in which a radiopaque material is encapsulated between polymer coatings.

10. A catheter formed by the process, comprising:
    a. dip coating a mandrel from a solution of an expandable, hydrophilic polymer;
    b. expanding the polymer coating away from the mandrel by contacting the polymer with a liquid containing water; and,
    c. removing the polymer coating in the form of a catheter from the mandrel, the catheter defining a longitudinal cavity approximating the shape of the mandrel; the catheter being adapted for insertion over a needle along the longitudinal cavity of the catheter, and upon drying to contract the catheter about the needle, the catheter being expandable due to contact with a liquid containing water, and thereby being removable from the needle;
    the catheter providing a bore size of about 12–30 gauge, a wall thickness of about 5–12 mils, a length of about ½"–6", and a hardness of about at least 90 SHORE A in the dry state.

11. The catheter of claim 10, in combination with the needle inserted therethrough.

12. The catheter of claim 10, in which the catheter provides a size conformation with the needle of less than about 1 mil.

13. The catheter of claim 10, in combination with a luer-lock hub connected by a flexible, plastic tube.

14. The combination of claim 13, in which the plastic tube is constructed of a clear material.

15. The catheter of claim 10, in combination with a luer-lock hub.

16. The combination of claim 15, in which the catheter provides a size conformation with the needle of less than about 1 mil.

17. The combination of claim 16, in which the luer-lock hub and catheter are connected by a flexible plastic tube.

18. The combination of claim 17, in which the plastic tube is constructed of a clear material.

19. The catheter of claim 10, containing a time release medication adapted for subsequent leaching out by passage of I.V. fluid, body tissue fluid and blood.

20. The catheter of claim 19, the said medication comprising a disinfectant, bacteriostat, fungicide and antibiotic.

21. The catheter of claim 10, in which a radiopaque material is encapsulated between polymer coatings.

* * * * *